| United States Patent [19] | [11] | 4,136,077 |
|---|---|---|
| Williams et al. | [45] | Jan. 23, 1979 |

[54] REACTION PRODUCT OF OLEFINICALLY-UNSATURATED NITRILE AND A MONOOLEFINIC HYDROCARBON AS PLASTICIZER FOR CONJUGATED DIENE-UNSATURATED NITRILE RUBBER

[75] Inventors: Ralph P. Williams; William S. Howard, both of Bartlesville, Okla.

[73] Assignee: Phillips Petroleum Company, Bartlesville, Okla.

[21] Appl. No.: 861,374

[22] Filed: Dec. 16, 1977

[51] Int. Cl.$^2$ .................................................. C08K 5/16
[52] U.S. Cl. .................................................. 260/32.4
[58] Field of Search ........................ 260/465.8 R, 32.4

[56] References Cited

U.S. PATENT DOCUMENTS

| 2,319,634 | 5/1943 | Sauser | 260/34.2 |
| 2,381,248 | 8/1945 | Bascom | 260/34.2 |
| 2,437,538 | 3/1948 | Kelly | 260/34.2 |
| 3,646,168 | 2/1972 | Barrett | 260/34.2 |
| 3,985,786 | 10/1976 | Drake | 260/265.8 R |

*Primary Examiner*—Paul R. Michl

[57] ABSTRACT

A reaction product of an olefinically unsaturated nitrile and a monoolefinic hydrocarbon containing an allylic hydrogen atom is used as plasticizer for a conjugated diene-unsaturated nitrile rubber.

7 Claims, No Drawings

REACTION PRODUCT OF OLEFINICALLY-UNSATURATED NITRILE AND A MONOOLEFINIC HYDROCARBON AS PLASTICIZER FOR CONJUGATED DIENE-UNSATURATED NITRILE RUBBER

This invention relates to plasticizing of conjugated diene-unsaturated nitrile rubber. It also relates to plasticizers for a conjugated diene-unsaturated nitrile rubber. In one of its aspects the invention relates to the use of certain nitrile-olefinic hydrocarbon reaction products as plasticizers for synthetic rubbers prepared from unsaturated nitrile.

In one of its concepts the invention provides a composition comprising a conjugated diene-unsaturated nitrile rubber and a plasticizing amount of a reaction product obtained by reacting an olefinically-unsaturated nitrile with a monoolefinic hydrocarbon containing an allylic hydrogen atom. In one of its specific concepts the invention provides for the plasticization of a conjugated diene-unsaturated nitrile rubber with a reaction product of isobutylene and acrylonitrile. In another more specific aspect the invention provides for the plasticization of a rubbery copolymer of a conjugated diene, e.g., butadiene or isoprene and an unsaturated nitrile, e.g., acrylonitrile, employing as plasticizer a reaction product of isobutylene and acrylonitrile.

Butadienes can be polymerized either alone or in the presence of other unsaturated compounds copolymerizable therewith to form polymers resembling natural rubber. To employ these synthetic rubbers softeners or plasticizers must be incorporated therein; often in larger amounts than are ordinarily used in natural rubber compositions. The softening of synthetic rubber has in general presented problems not encountered in the softening of natural rubber due to its different behavior on roll mills, incompatibility of synthetic rubber with certain softening and plasticizing materials commonly employed in natural rubber, and other differences in performance properties and costs. It has been particularly difficult to find satisfactory low cost softeners or plasticizers for the oil-resisting synthetic rubbers such as copolymers of butadiene and acrylonitrile and plastic polymers of chloroprene.

The high degree of oil resistance of nitrile rubber limits the selection to certain types of plasticizers. Ester types, aromatic oils, and polar-type derivatives are generally used. Two of the major factors affecting the compatibility of ester-type plasticizers in nitrile rubber are the type of plasticizer and the acrylonitrile content of the rubber. The degree of compatibility decreases as the acrylonitrile content increases. A plasticizer which can be used at 30 parts per hundred (phr) in a low-acrylonitrile content rubber may bleed if added in the same amount to a high-acrylonitrile content rubber. Such a plasticizer may be satisfactory, however, if used in combination with a second, more compatible plasticizer.

In compounding for good low-temperature properties, best results are usually obtained with a combination of two or three ester-type plasticizers. Unfortunately, the ester-type plasticizers are often extracted when the final rubber is in contact with certain fuels and oils. At times, this extraction is not critical. However, it will be objectionable where shrinkage of the final rubber or part can not be tolerated and where contamination of the immersing medium is undesirable.

We have now conceived that a reaction product obtained when an olefinically-unsaturated nitrile and a monoolefinic hydrocarbon containing an allylic hydrogen atom are thermally contacted, producing unsaturated dinitriles and oligomers of the unsaturated dinitriles that there is produced a very satisfactory plasticizer for conjugated diene-unsaturated nitrile rubber.

It is an object of this invention to produce a plasticizer for a conjugated diene-unsaturated nitrile rubber. It is another object of this invention to produce a plasticized conjugated diene-unsaturated nitrile rubber. It is a further object of the invention to produce a plasticized butadiene-acrylonitrile rubber. A further object of the invention is to produce an isoprene-acrylonitrile rubber containing composition, also containing a plasticizer.

Other aspects, concepts, objects and the several advantages of this invention are apparent from a study of this disclosure and the appended claims.

According to the invention a product obtained when an olefinically unsaturated nitrile and a monoolefinic hydrocarbon containing an allylic hydrogen atom are thermally contacted to produce unsaturated dinitriles and oligomers of the unsaturated dinitriles is incorporated in a conjugated diene-olefinically unsaturated nitrile copolymer to provide its plasticization.

Further, according to the present invention, there is produced a plasticized-conjugated diene-unsaturated nitrile rubber containing a plasticizing amount of a reaction product obtained when an olefinically unsaturated nitrile and a monoolefinic hydrocarbon, containing an allylic hydrogen atom, are thermally contacted producing unsaturated dinitriles and oligomers of the unsaturated dinitrile.

Still further according to the invention, a composition comprising a copolymer of conjugated diene, e.g., butadiene and/or isoprene and an unsaturated nitrile, e.g., acrylonitrile, and a plasticizer, e.g., the reaction product of isobutylene and acrylonitrile, which may include one or more of the unsaturated diadduct dinitriles, 5-methyl-4-nonenedinitrile and 5-methylenenonanedinitrile and corresponding isomers and oligomers of these dinitriles.

The reaction product or mixtures of the components thereof are the plasticizers of this invention.

In one embodiment of this invention it provides a new type of plasticizer based on an olefinically unsaturated nitrile and monoolefinic hydrocarbon containing an allylic hydrogen atom which can be employed with a synthetic rubber prepared by the polymerization of a conjugated diene and an olefinically unsaturated nitrile, referred to as "nitrile rubber." Another embodiment of this invention provides a plasticizer which aids in the production of vulcanizates having good performance in properties tests such as elongation, tensile strength, modulus and durometer hardness.

The preparation of a diadduct dinitrile employed in this invention can be carried out according to the disclosure of U.S. Pat. No. 3,985,786 wherein an olefinically unsaturated nitrile having the general formula (I) 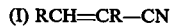

and a monoolefinic hydrocarbon containing an allylic hydrogen atom and represented by the formula (II) 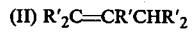

are thermally contacted to produce an unsaturated "diadduct" product having the formula

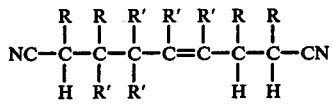
(III)

wherein each R is independently selected from the group consisting of hydrogen and hydrocarbyl radicals. Preferably, the hydrocarbyl radicals are selected from the group consisting of alkyl, cycloalkyl, and aryl hydrocarbyl radicals and combinations thereof, such as alkylcycloalkyl, cycloalkylalkyl, aralkyl and arylcycloalkyl radicals. Each R' is independently selected from the group consisting of hydrogen and hydrocarbyl radicals, said hydrocarbyl radicals being selected from the group consisting of alkyl, cycloalkyl, and aryl hydrocarbyl radicals and combinations thereof. Preferred are those monoolefinic hydrocarbons having 3 to 12 carbon atoms and having an alkyl group, preferably methyl, as a side chain attached to at least one of the carbon atoms comprising the ethylenic linkage.

Examples of unsaturated nitriles (I) are acrylonitrile, methacrylonitrile, 2-decenenitrile, 3-cyclohexyl-2-propenenitrile, 4-phenyl-2-butenenitrile, 3(p-tolyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile, and the like, and mixtures thereof.

Specific examples of olefinically unsaturated hydrocarbons (II) containing allylic hydrogen atoms which are employed in the preparation of dinitriles useful in this invention include propylene, isobutylene, diisobutylene, triisobutylene, 1,5-hexadiene, beta-pinene, 1,5-cyclooctadiene, 2,4,4-trimethyl-1-pentene, 2-butene, biallyl, bimethallyl, alpha-methyl-styrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene, and the like, and mixtures thereof.

Examples of a diadduct (III) reaction product obtained from the heretofore mentioned olefinically unsaturated nitriles such as acrylonitrile and an olefinic hydrocarbon containing an allylic hydrogen atom such as isobutylene is the reaction product mixture consisting of the major isomer species 5-methylenenonanedinitrile and 5-methyl-4-nonenedinitrile, that contains minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

The diadduct products of this invention can be used in the broad range of from about 1 to about 100 parts per hundred (phr) nitrile rubber to effect plasticization. The range from about 3 to about 20 phr is now generally preferred, particularly when nitrile rubber-based formulations are vulcanizates and also contain significant amounts of other ingredients such as fillers, reinforcing agents, curing agents, pigments, etc.

OLIGOMERS OF UNSATURATED DIADDUCT DINITRILES

Oligomers of unsaturated dinitriles useful in this invention are generally obtained as by-product kettle residues during the distillation of the unsaturated diadduct dinitriles. These oligomers are represented by the formula

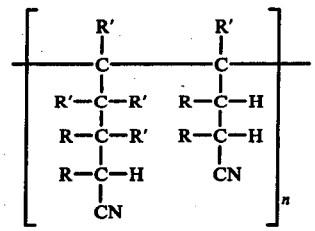

wherein R and R' are as defined earlier and n can be 2 to 20 but preferably 3 to 6. The oligomer products of this invention can be used in the broad range of from about 1 to about 100 phr nitrile rubber to effect plasticization. The range of from about 3 to about 20 is generally preferred, particularly when nitrile rubber-based formulations are vulcanizates and also contain significant amounts of other ingredients such as fillers, reinforcing agents, curing agents, pigments, etc. The oligomer products can also be used admixed with the unsaturated dinitrile monomers at any proportions required to produce satisfactory performance properties.

Nitrile rubbers employed in this invention and to which are added the dinitrile and/or dinitrile oligomer plasticizers of this invention can be defined as copolymers of conjugated dienes such as butadiene and isoprene and an unsaturated nitrile such as acrylonitrile. These kinds of nitrile rubbers are known and to an extent are produced under various trade names as listed below. The invention is in the provision of a plasticizer. Accordingly, it is not limited to the recited nitrile rubbers.

| Nitrile Rubber Trade Name | Source |
|---|---|
| Hycar | B. F. Goodrich Chemical Co. |
| Chemigum | Goodyear Tire and Rubber Co. |
| Paracil | Uniroyal Chemicals |
| Butaprene | Firestone Tire and Rubber Co. |
| Krynac | Polymer Corporation (Canada) |
| Perbunan | Mobay Chemicals |
| Hycar | British Geon Limited |

Fillers and additives to be used in nitrile rubber vulcanizates described in this invention can be supplied by those skilled in the art. Among such are zinc oxide, stearic acid, carbon black, elemental sulfur, accelerator catalysts, stabilizers, epoxides of soybean oil, etc.

The formulations of this invention can be prepared in any convenient manner by those skilled in the art.

A method employed to prepare formulations according to the invention is to mix all recipes in a laboratory Midget Banbury operating at 120 rpm at 177° C. for 2 to 3 minutes and to sheet off on a 7.62 cm (3 in.) × 17.78 cm (7 in.) roll mill.

Testing

Test specimens were compression molded at 153° C. for 30 mins. at 4.44 kN (1000 lbs.) force and tested in accordance with appropriate ASTM procedures or slight modifications thereof.

EXAMPLE I

A standard nitrile rubber recipe (Chemigum Brochure TN5697) was used to compare performance properties of formulations employing different plasticizers. This recipe is listed as follows:

| Component | Chemical or Trade Name | Parts by Weight |
|---|---|---|
| Nitrile Rubber[a] | Chemigum N615 | 100 |
| Zinc Oxide | — | 5 |
| Stearic Acid | — | 0.5 |
| Antioxidant[b] | Agerite Resin D | 2 |
| Reinforcing Agent | Carbon Black (FEF) N550 | 70 |
| Plasticizer A[c] | Paraplex G60-Polyester | 3 |
| Plasticizer B | -Variable- | 5 and 10 |
| Elemental Sulfur | — | 0.25 |
| Accelerator A[d] | Methyl Tuads | 3 |
| Accelerator B[e] | Vultrol | 1 | a) Butadiene/acrylonitrile copolymer, 45-63 Mooney Viscosity ML-4 at 100° C
b) Polymerized 1,2-dihydro-2,2,-4-trimethylquinoline
c) Soybean oil epoxide
d) Tetramethyl thiuram disulfide
e) N-Nitrosodiphenylamine Dioctyl phthalate (DOP) was used in the above recipe as the control plasticizer for comparison with the compositions using the plasticizers of the invention. For illustrative purposes, plasticizers of the invention were those based on the reaction products of isobutylene and acrylonitrile as herein described, namely, the unsaturated diadduct dinitriles, 5-methyl-4-nonenedinitrile and 5-methylenenonanedinitrile and corresponding isomers and the oligomers of these dinitriles. These unsaturated diadduct dinitriles are referred to as a single product, MNDN, and are obtained from a distillation of the reaction mass herein described and in the above-mentioned patent, the disclosure of which is incorporated by reference. The oligomer products are essentially the kettle bottoms or residue from the above distillation and will vary in composition depending upon distillation efficiency from 0 to about 20% undistilled diadduct dinitrile & 80–100% of a residue considered, by analysis (see below), to be the tetramer of the diadduct dinitrile.

| Oligomer Analysis | Calculated For $C_{40}H_{52}N_7$ | Experimentally Found |
|---|---|---|
| Wt. % Carbon | 76.1 | 75.2 |
| Wt. % Hydrogen | 8.3 | 8.4 |
| Wt. % Nitrogen | 15.6 | 15.7 |
| Total | 100.0 | 99.3 |
| Molecular Weight | 631 | 629 |

The above recipe with the corresponding plasticizer was blended for 2 to 3 minutes in a hot (177° C.) laboratory Midget Banbury (120 rpm) and sheeted off on a 7.62 cm (3 in.) × 17.78 cm (7 in.) roll mill. The material was compression molded at 153° C. for 30 mins. at 4.44 kN (1000 lbs.) force and cut into the sizes appropriate for the specific ASTM test. These results are shown below in Table I.

Table I

| | Plasticizer Employed | | | | | |
|---|---|---|---|---|---|---|
| | DOP | | MNDN | | Oligomer | |
| | 5 pts. | 10 pts. | 5 pts. | 10 pts. | 5 pts. | 10 pts. |
| 1. Mooney, ML-4 at 100° C | 102 | 81 | 101 | 80 | 106 | 90 |
| 2. Scorch at 121° C, min. Mooney | 62.0 | 49.4 | 63.9 | 53.0 | 63.8 | 54.3 |
| 5 Point Rise, minutes | 13.3 | 14.8 | 12.6 | 12.9 | 13.0 | 12.5 |
| 3. Cure Rate Index* | 10.0 | 9.5 | 11.1 | 11.1 | 10.6 | 11.8 |
| 4. 90% Cure, minutes* | 12.6 | 13.1 | 11.6 | 11.6 | 12.1 | 10.8 |
| Vulcanizate** | | | | | | |
| 5. 300% Modulus, psi | 3090 | 2790 | 3150 | 2800 | 3120 | 2705 |
| , MPa | 21.30 | 19.23 | 21.72 | 19.30 | 21.51 | 18.65 |
| 6. Tensile Strength, psi | 3150 | 3010 | 3000 | 2750 | 3135 | 2910 |
| , MPa | 21.72 | 20.75 | 20.68 | 18.96 | 21.62 | 20.06 |
| 7. Elongation, % | 300 | 330 | 280 | 310 | 280 | 320 |
| 8. Shore A Hardness | 72 | 69.5 | 72 | 70.5 | 73 | 72.5 |
| 9. Compression Set, % | 5.2 | 5.6 | 4.3 | 4.7 | 4.3 | 4.6 |
| 10. Brittleness Temp., C | −30 | −31 | −33 | −34 | −28 | −29 |
| 11. Gehman Freeze Point, C | −28 | −31 | −32 | −37 | −27 | −29 |
| 12. Tensile Strength, Aged 70 hrs. | | | | | | |
| a. In air at 125° C, psi*** | 3000 | 2810 | 3030 | 2700 | 3050 | 3100 |
| , MPa | 20.68 | 19.37 | 20.89 | 18.62 | 21.03 | 21.37 |
| b. In ASTM Oil #1 at 150° C, psi | 3190 | 3070 | 3000 | 3030 | 3270 | 2860 |
| , MPa | 21.99 | 21.17 | 20.68 | 20.89 | 22.55 | 19.72 |
| 13. Elongation, %, Aged 70 hrs. | | | | | | |
| a. In air at 125° C*** | 180 | 185 | 180 | 190 | 180 | 215 |
| b. In ASTM Oil #1 at 150° C | 235 | 250 | 225 | 240 | 260 | 255 |

*Monsanto Rheometer at 151.7° C
**Cured 15 mins. at 151.7° C
***Cured 10 mins. at 151.7° C

EXAMPLE II

An alternate nitrile rubber recipe was employed to further compare the adduct dinitrile MNDN and oligomers as plasticizers. This recipe differs from that in Example I in that a different nitrile rubber and accelerator B is employed and only one plasticizer is used. This formulation, listed below, was mixed and samples prepared in the same manner as previously described. The test results are shown in Table II.

| Component | Chemical or Trade Name | Parts by Weight |
|---|---|---|
| Nitrile Rubber[a] | Chemigum N318B | 100 |
| Zinc Oxide | — | 5 |
| Stearic Acid | — | 0.5 |
| Antioxidant | Agerite Resin D | 2 |
| Reinforcing Agent | Carbon Black (FEF), N-550 | 70 |
| Plasticizer | -Variable- | 5 to 10 |
| Elemental Sulfur | — | 0.4 |
| Accelerator A[a] | Methyl Tuads | 2 |
| Accelerator B[b] | NOBS special | 1 |

[a]Butadiene/acrylonitrile copolymer, 70-80 Mooney Visc.
[b]N-Oxydiethylene benzothiazole-2-sulfenamide Table II

|  | Plasticizer | | |
| --- | --- | --- | --- |
|  | 5 pts. DOP | 5 pts. Oligomer | 5 pts. DOP + 3 pts. Oligomer |
| 1. Mooney, MS-4 at 100° C | 55 | 59.5 | 49 |
| 2. Scorch at 121° C, minimum Mooney | 70.0 | 70.7 | 60.9 |
| 5 Point Rise, minutes | 14.1 | 11.4 | 13.7 |
| 3. Cure Rate Index | 20.4 | 21.7 | 18.9 |
| 4. 90% Cure, minutes | 7.8 | 7.3 | 7.9 |
| Vulcanizate* | | | |
| 5. 200% Modulus, psi | 2220 | 2225 | 2025 |
| , MPa | 15.31 | 15.34 | 13.96 |
| 6. Tensile Strength, psi | 3060 | 3000 | 2830 |
| , MPa | 21.10 | 20.68 | 19.51 |
| 7. Elongatoin, % | 290 | 290 | 290 |
| 8. Shore A Hardness | 78 | 78 | 77.5 |
| 9. Gehman Freeze Pont**, C | −27 | −27 | −31 |
| 10. Tensile Strength, Aged 70 hrs. | | | |
| a. In air at 100° C, psi | 3090 | 3220 | 3090 |
| , MPa | 21.30 | 22.2 | 21.30 |
| b. In ASTM Oil #1, psi | 2880 | 3080 | 2980 |
| , MPa | 19.86 | 21.24 | 20.55 |

*Cured 20 mins. at 151.7° C
**Cured 15 mins. at 151.7° C

EXAMPLE III

Another alternate nitrile rubber composition was employed to further illustrate the properties of compounded rubber when mixtures of MNDN and oligomers are used as plasticizers in cured nitrile rubber compositions. The compositions were mixed and specimens prepared as previously described. The recipe is shown below along with the experimental results listed in Table III.

| Component | Chemical or Trade Name | Parts by Weight |
| --- | --- | --- |
| Nitrile Rubber | Chemigum N615 | 100 |
| Zinc Oxide | — | 5 |
| Stearic Acid | — | 0.5 |
| Antioxidant | Agerite Resin D | 2 |
| Reinforcing Agent | Carbon Black (FEF) | 70 |
| Plasticizer | -Variable- | 5 |
| Elemental Sulfur | | 0.4 |
| Accelerator A | Methyl Tuads | 2 |
| Accelerator B | NOBS Special | 1 |

Table III

|  | 5 pts. Plasticizer | | | |
| --- | --- | --- | --- | --- |
|  | DOP | Oligomer | 10% MNDN + 90% Oligomer | 15.5% MNDN + 84.5% Oligomer |
| 1. Mooney, MS-4 at 100° C | 54 | 58 | 60 | 61 |
| 2. Scorch at 121° C, minimum Mooney | 36.3 | 36.2 | 37.1 | 36.2 |
| 5 Point Rise, minutes | 16.0 | 12.4 | 13.5 | 14.0 |
| 3. Cure Rate Index | 19.2 | 18.5 | 18.5 | 18.2 |
| 4. 90% Cure, minutes | 8.4 | 8.0 | 8.3 | 8.5 |
| Vulcanizate* | | | | |
| 5. 200% Modulus, psi | 2743 | 2758 | 2409 | 2351 |
| , MPa | 18.86 | 18.96 | 16.56 | 16.16 |
| 6. Tensile Strength, psi | 3106 | 3120 | 3164 | 3149 |
| , MPa | 21.35 | 21.45 | 21.75 | 21.65 |
| 7. Elongation, % | 230 | 240 | 280 | 300 |
| 8. Shore A Hardness | 78 | 79 | 79 | 78 |
| 9. Tensile Strength, Aged 70 hrs. | | | | |
| a. In air at 100° C, psi | 3110 | 3370 | 3210 | 3222 |
| , MPa | 21.38 | 23.17 | 22.07 | 22.15 |
| b. In ASTM Oil #1 at 100° C, psi | 3020 | 3150 | 3250 | 3110 |
| , MPa | 20.76 | 21.66 | 22.34 | 21.38 |
| 10. Elongation, %, Aged 70 hrs. | | | | |
| a. In air at 100° C | 225 | 260 | 280 | 265 |
| b. In ASTM Oil #1 | 230 | 235 | 245 | 255 |

*Cured 20 mins. at 151.7° C

Basically, the results in Tables I and II show that MNDN (distilled) or the tetramer oligomer of MNDN have utility as a plasticizer in a nitrile rubber formulation, nitrile rubbers being generally difficult to plasticize. In addition MNDN (distilled) or the MNDN oligomer are good alternates for the commonly used dioctyl phthalate. Rubber scorch time is slightly shortened but major performance properties such as modulus, hardness and oil resistance are not significantly affected. The MNDN diadduct improves low temperature flexibility as evidenced by a lower brittleness temperature.

The results from Table III indicate that mixtures of blends of MNDN and MNDN oligomers can be employed with equally good results.

Reasonable variation and modification are possible within the scope of the foregoing disclosure and the appended claims to the invention the essence of which is that the thermal reaction product of an olefinically unsaturated nitrile and a monoolefinic hydrocarbon containing an allylic hydrogen atom, comprising unsaturated dinitriles and oligomers of the unsaturated dinitriles has been provided as a plasticizer for conjugated diene-unsaturated nitrile rubber.

I claim:

1. A conjugated diene-unsaturated nitrile rubber plasticized with at least one reaction product of an olefinically unsaturated nitrile, having the general formula $$(I) \quad RCH=CR-CN$$

and a monoolefinic hydrocarbon, containing an allylic hydrogen atom and represented by the formula (II) R′$_2$C=CR′CHR′—$_2$, which have been thermally contacted to produce an unsaturated diadduct product having the formula

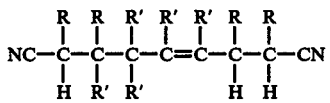 (III)

wherein each R and each R′ is independently selected from the group consisting of hydrogen and hydrocarbyl radicals, and an oligomer thereof, which can be represented by the formula

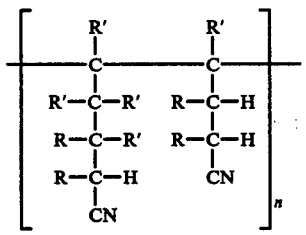

wherein R and R′ are as defined earlier and n is equal to an integer in the range 2 to 20.

2. A composition according to claim 1 wherein R and R′ are selected from the group consisting of alkyl, cycloalkyl, aryl hydrocarbyl radicals and combinations thereof.

3. A composition according to claim 2 wherein the nitrile is at least one selected from the acrylonitrile, methacrylonitrile, 2-decenenitrile, 3-cyclohexyl-2-propenenitrile, 4-phenyl-2-butenenitrile, 3-(p-tolyl)-2-propenenitrile, 2-butenenitrile, 2-hexenenitrile, 5-methyl-2-hexenenitrile, 4-methyl-2-heptenenitrile, 6,6,8,8,-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile.

4. A composition according to claim 2 wherein in the olefinically unsaturated hydrocarbon is propylene, isobutylene, diisobutylene, 1,5-hexadiene, beta-pinene, 1,5-cyclooctadiene, 2,4,4-trimethyl-1-pentene, 2-butene, biallyl, bimethallyl, alpha-methyl-styrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene.

5. A composition according to claim 1 wherein the rubber is butadiene-acrylonitrile rubber and the plasticizer is at least one reaction product of isobutylene and acrylonitrile.

6. A composition according to claim 1 wherein the plasticizer is at least one 5-methyl-4-nonenedinitrile and 5-methylene nonanedinitrile and corresponding isomers and oligomers thereof.

7. A composition according to claim 1 wherein the plasticizer is at least a portion of the oligomer kettle product obtained from the distillation of the reaction mass in which isobutylene and acrylonitrile have been reacted to produce unsaturated diadduct dinitriles, 5-methyl-4-nonenedinitrile and 5-methylene nonanedinitrile and corresponding isomers and oligomers thereof.

* * * * *